under 35 U.S.C. 154(b) by 24 days.

(12) United States Patent
Yang et al.

(10) Patent No.: US 8,586,790 B2
(45) Date of Patent: Nov. 19, 2013

(54) ANHYDRIDE DERIVATIVES OF 2-(S)-(6-METHOXY-2-NAPHTYL)-PROPANOIC ACID, PREPARATION METHOD AND USE THEREOF

(75) Inventors: Hao-Cheng Yang, Taoyuan (TW); Chia-Chung Tsai, Taoyuan (TW); Chi-Hsiang Yao, Taoyuan (TW)

(73) Assignee: Everlight USA, Inc., Pineville, NC (US)

( * ) Notice: Subject to any disclaimer, the term of this patent is extended or adjusted under 35 U.S.C. 154(b) by 24 days.

(21) Appl. No.: 13/368,601

(22) Filed: Feb. 8, 2012

(65) Prior Publication Data

US 2012/0226068 A1 Sep. 6, 2012

(30) Foreign Application Priority Data

Mar. 1, 2011 (TW) ................. 10016621 A

(51) Int. Cl.
*C07C 53/00* (2006.01)
(52) U.S. Cl.
USPC ........................................ 562/887

(58) Field of Classification Search
None
See application file for complete search history.

(56) References Cited

U.S. PATENT DOCUMENTS

2005/0234123 A1   10/2005   Belli et al.
2006/0173005 A1*  8/2006    Del Soldato et al. ...... 514/237.5

FOREIGN PATENT DOCUMENTS

| WO | 95/09831 A1 | 4/1995 |
| WO | 98/25918 A1 | 6/1998 |
| WO | 01/10814 A1 | 2/2001 |
| WO | 2009/149053 A2 | 12/2009 |

* cited by examiner

*Primary Examiner* — Karl J Puttlitz
(74) *Attorney, Agent, or Firm* — Turocy & Watson, LLP

(57) ABSTRACT

The present invention provides a novel anhydride derivative of 2-(S)-(6-methoxy-2-naphtyl)-propanoic acid for preparing nitrooxyalkyl esters of 2-(S)-(6-methoxy-2-naphtyl)-propanoic acid with high purity to meet requirements of the industry.

14 Claims, No Drawings

ANHYDRIDE DERIVATIVES OF 2-(S)-(6-METHOXY-2-NAPHTYL)-PROPANOIC ACID, PREPARATION METHOD AND USE THEREOF

BACKGROUND OF THE INVENTION

1. Field of the Invention

The present invention relates to an anhydride derivative, and more particularly, to a anhydride derivative of 2-(S)-(6-methoxy-2-naphtyl)-propanoic acid, a preparation method and a use thereof.

2. Description of Related Art

Nonsteroidal anti-inflammatory drugs (NSAIDs) such as 2-(S)-(6-methoxy-2-naphtyl)-propanoic acid (Naproxen) are anti-inflammatory agents, analgesics and fever reducers, and thus play an important role in treating diseases. However, due to the gastrointestinal side effects, NSAIDs are not used for long term treatments. WO95/09831 discloses nitric esters of NSAIDs including 2-(S)-(6-methoxy-2-naphtyl)-propanoic acid 4-nitrooxybutyl ester (Naproxcinod), which has anti-inflammation and pain-relieving activities, is of good tolerance, and also reduces the gastrointestinal side effects. Naproxcinod (also named as NO-naproxen, AZD-3582, HCT-3012C or nitronaproxen) is a cyclooxygenase-inhibiting nitric oxide donator (CINOD), which reduces the gastrointestinal side effects resulting from Naproxen and lowers blood pressure via nitric oxide (NO) release.

WO95/09831 discloses the preparation of Naproxcinod, by the reaction of the sodium salt of Naproxen and halobutanol, or the reaction of the sodium salt of Naproxen and 1,4-dihalobutane and the nitration with silver nitrate, so as to obtain Naproxcinod. WO98/25918 and WO2001/010814 disclose the preparation of Naproxcinod by using acyl halides of Naproxen. WO2004/020384 discloses the preparation of Naproxcinod by using salts of Naproxen. WO03/045896 discloses the preparation of Naproxcinod from the reaction of a sulfonate ester and Naproxen, halides or salts thereof. WO2009/149053 discloses the preparation of Naproxcinod from the reaction of 1,4-dihalobutane and Naproxen, halides or salts thereof. However, the acyl halides of Naproxen are not chemically stable, and easily racemized. Further, the above-mentioned conventional methods are complicated in steps, the temperature control and the long duration, and the yield is only 70% to 80%. Moreover, the products in the conventional method need to be further purified for obtaining high purity of Naproxcinod. In addition, the cost of the conventional methods is high due to the usage of silver nitrate or chromatography.

Hence, there is a need to provide a preparation method for obtaining Naproxcinod with high purity and high yield.

SUMMARY OF THE INVENTION

The present invention provides an anhydride derivative of 2-(S)-(6-methoxy-2-naphtyl)-propanoic acid of formula (I) (abbreviated as the compound of formula (I), hereafter):

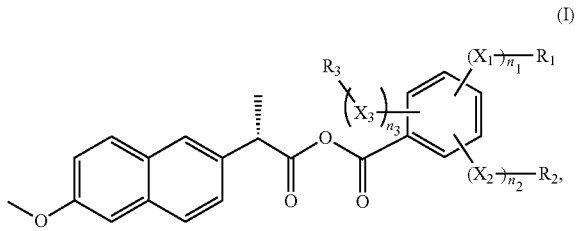

(I)

wherein $X_1$, $X_2$ and $X_3$ are independently —NR'—, —O— or —S—; $n_1$, $n_2$ and $n_3$ are independently 0 or 1; and $R_1$, $R_2$, $R_3$ and R' are independently hydrogen, a linear or branched $C_{1-10}$alkyl or halo$C_{1-10}$alkyl.

The present invention further provides the use of the compound of formula (I) for preparing a nitrooxyalkyl ester derivative. In one embodiment, the nitrooxyalkyl ester derivative is a propanoic acid derivative. In one embodiment, the nitrooxyalkyl ester derivative is a nitrooxyalkyl ester derivative of 2-(S)-(6-methoxy-2-naphtyl)-propanoic acid. In one embodiment, the nitrooxyalkyl ester derivative is a nitrooxybutyl ester of 2-(S)-(6-methoxy-2-naphtyl)-propanoic acid.

The present invention further provides a method for preparing a nitrooxybutyl ester of 2-(S)-(6-methoxy-2-naphtyl)-propanoic acid. The method includes the steps of performing a reaction of 2-(S)-(6-methoxy-2-naphtyl)-propanoic acid and a compound of formula (a) to form a compound of formula (I):

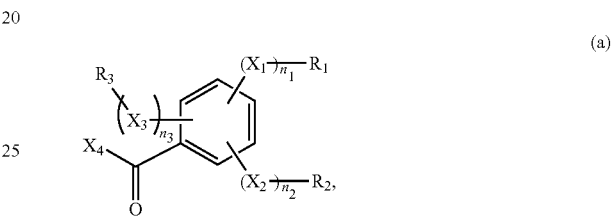

(a)

wherein $X_1$, $X_2$ and $X_3$ are independently —NR'—, —O— or —S—; $n_1$, $n_2$ and $n_3$ are independently 0 or 1; $R_1$, $R_2$, $R_3$ and R' are independently hydrogen, a linear or branched $C_{1-10}$alkyl or halo$C_{1-10}$alkyl; and $X_4$ is a halogen; and performing a reaction of the compound of formula (I) and 1,4-butanediol mononitrate.

In one embodiment, the 1,4-butanediol mononitrate is prepared by using a nitrating agent to nitrify a compound of formula (i) to obtain a compound of formula (ii),

RC(O)O—(CH$_2$)$_4$—OH     (i)

RC(O)O—(CH$_2$)$_4$—ONO$_2$     (ii)

wherein R is a linear or branched $C_{1-5}$alkyl; and performing a reaction of the compound of formula (ii) and an inorganic alkali to obtain the 1,4-butanediol mononitrate.

DETAILED DESCRIPTION OF THE PREFERRED EMBODIMENTS

The detailed description of the present invention is illustrated by the following specific examples. Persons skilled in the art can conceive the other advantages and effects of the present invention based on the disclosure contained in the specification of the present invention.

"Alkyl" herein refers to a branched or linear aliphatic hydrocarbon group. The term "$C_{1-10}$alkyl" herein refers to an alkyl having 1 to 10 carbon atoms. The alkyl may be, but not limited to, methyl, ethyl, propyl, isopropyl, butyl, isobutyl, sec-butyl, tert-butyl, pentyl, 2-pentyl, isopentyl, neopentyl, hexyl, 2-hexyl, 3-hexyl, isohexyl, 2-ehtylbutyl, heptyl, octyl, nonyl, decyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 1,1-dimethylbutyl, 2,2-dimethylbutyl, 3,3-dimethylbutyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimthylhexyl, 4,4-dimethylhexyl, 2-ethylpentyl, 3-ethylpentyl, 2-ethylhexyl, 3-ethylhexyl, 4-ethylhexyl, 2-methyl-2ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl, etc.

In the specification of the present invention, "halogen" refers to F, Cl, Br or I.

The present invention provides a compound of formula (I):

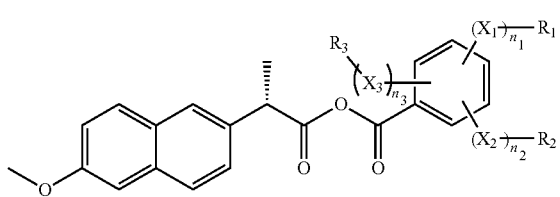

(I)

wherein $X_1$, $X_2$ and $X_3$ are independently —NR'—, —O— or —S—; $n_1$, $n_2$ and $n_3$ are independently 0 or 1; and $R_1$, $R_2$, $R_3$ and R' are independently hydrogen, a linear or branched $C_{1-10}$alkyl or halo$C_{1-10}$alkyl.

In one embodiment, at least one of $X_1$, $X_2$ and $X_3$ is —O—. In one embodiment, at least one of $X_1$, $X_2$ and $X_3$ is —O—, and the corresponding $R_1$, $R_2$ or $R_3$ is methyl.

In one embodiment, $n_1$, $n_2$ and $n_3$ are independently 0, and $R_1$, $R_2$ and $R_3$ are independently hydrogen.

In the present invention, the compound of formula (I) is used for preparing a nitrooxyalkyl ester derivative, wherein the alkyl group is $C_{1-10}$alkyl, preferably $C_{1-5}$alkyl, and more preferably $C_{3-5}$alkyl. In one embodiment, the compound of formula (I) is used for preparing a nitric ester derivative of NSAIDs (for example, but not limited to, a propanoic acid derivative such as 2-(S)-(6-methoxy-2-naphtyl)-propanoic acid). In one embodiment, the compound of formula (I) is used for preparing a nitrooxyalkyl ester derivative of 2-(S)-(6-methoxy-2-naphtyl)-propanoic acid), which may be, but not limited to, a nitrooxybutyl ester of 2-(S)-(6-methoxy-2-naphtyl)-propanoic acid.

According to the present invention, the preparation of the nitrooxyalkyl ester derivative by using the compound of formula (I) can produce the crude product with high purity and high yield.

In the present invention, the method for preparing a nitrooxybutyl ester of 2-(S)-(6-methoxy-2-naphtyl)-propanoic acid includes performing a reaction of 2-(S)-(6-methoxy-2-naphtyl)-propanoic acid and a compound of formula (a) to form a compound of formula (I)

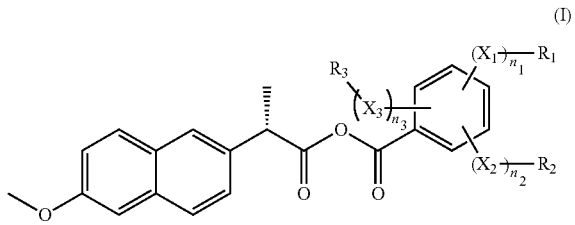

(I)

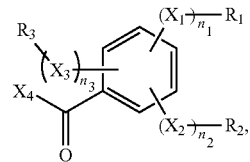

(a)

wherein $X_1$, $X_2$ and $X_3$ are independently —NR'—, —O— or —S—; $n_1$, $n_2$ and $n_3$ are independently 0 or 1; $R_1$, $R_2$, $R_3$ and R' are independently hydrogen, a linear or branched $C_{1-10}$alkyl or halo$C_{1-10}$alkyl; and $X_4$ is a halogen; and performing a reaction of the compound of formula (I) and 1,4-butanediol mononitrate.

In one embodiment, $X_4$ is Cl in the compound of formula (a).

In one embodiment, at least one of $X_1$, $X_2$ and $X_3$ is —O— in the compound of formula (a). In one embodiment, at least one of $X_1$, $X_2$ and $X_3$ is —O—, and the corresponding $R_1$, $R_2$ or $R_3$ is methyl. For example, the compound of formula (a) is 4-methoxybenzoyl chloride.

In one embodiment, the compound of formula (a) is benzoyl chloride.

According to an embodiment of the present invention, the preparation of the nitrooxyalkyl ester derivative by using the compound of formula (I) can produce the crude product with high purity and high yield.

According to the present invention, the preparation of the nitrooxyalkyl ester derivative is performed in the presence of an alkali. The alkali may be, but not limited to, an inorganic alkali such as NaOH, KOH, Mg(OH)$_2$ and LiOH; an alkali salt such as Na$_2$CO$_3$, K$_2$CO$_3$, Cs$_2$CO$_3$, CaCO$_3$, NaHCO$_3$; an organic alkali such as triethylamine, diisopropylethylamine, tributylamine, cyclohexyldimethylamine, pyridine, methyl pyridine, 4-(dimethylamino)pyridine, N,N-dimethylaniline, N-methyl piperidine, N-methylpyrrolidine, N-methyl morpholine, 1,5-diazabicyclo[4.3.0]-5-nonene, 1,4-diazabicyclo[2.2.2]octane, 1,8-diazabicyclo(5.4.0)undec-7-ene, imidazoles, etc.

In an embodiment of the present invention, a nitrooxybutyl ester of 2-(S)-(6-methoxy-2-naphtyl)-propanoic acid is prepared by using 2-(S)-(6-methoxy-2-naphtyl)-propanoic acid in the presence of an alkali. The alkali may be triethylamine, diisopropylethylamine, 4-(dimethylamino)pyridine or the combination thereof.

According to an embodiment of the present invention, the reaction of 2-(S)-(6-methoxy-2-naphtyl)-propanoic acid and the compound of formula (a) is performed in the presence of diisopropylethylamine to form the compound of formula (I). In an embodiment of the present invention, the reaction of 2-(S)-(6-methoxy-2-naphtyl)-propanoic acid and the compound of formula (a) is performed in the presence of diisopropylethylamine, and then 1,4-butanediol mononitrate is added for preparing the nitrooxyalkyl ester of 2-(S)-(6-methoxy-2-naphtyl)-propanoic acid.

According to an embodiment of the present invention, the reaction of 2-(S)-(6-methoxy-2-naphtyl)-propanoic acid and the compound of formula (a) is performed in the presence of diisopropylethylamine to form the compound of formula (I), and the reaction of the compound of formula (I) and 1,4-butanediol mononitrate is performed in the presence of 4-(dimethylamino)pyridine to form the nitrooxybutyl ester derivative. According to an embodiment of the present invention, 2-(S)-(6-methoxy-2-naphtyl)-propanoic acid and the compound of formula (a) are added in the reactor to perform the reaction in the presence of diisopropylethylamine; 1,4-butanediol mononitrate is added in the reactor; and then 4-(dimethylamino)pyridine is used as a catalyst to prepare a nitrooxyalkyl ester derivative of 2-(S)-(6-methoxy-2-naphtyl)-propanoic acid.

The preparation method of the present invention is performed in a solvent. The solvent may be, but not limited to, an ether such as diethyl ether, isopropyl ether, diphenyl ether, tetrahydrofuran, 1,4-dioxane or 1,2-dimethoxyethane; an aromatic hydrocarbon such as benzene, chlorobenzene, toluene or xylene; a saturated hydrocarbon such as cyclohexane or hexane; an amide such as N,N-dimethylformamide, N,N-dimethylacetamide or hexamethylphosphoramide; a halohydrocarbon such as dichloromethane, trichloromethane (chloroform), tetrachloromethane, 1,2-dichloroethane, trichloroethane or tetrachloroethane; a nitrile such as acetonitrile or propanenitrile; a sulfoxide such as dimethyl sulfoxide; an organic aryl alkali such as pyridine or dimethylpyridine; an anhydride such as acetic anhydride; an ester such as methyl acetate, ethyl acetate or butyl acetate; or a ketone such as acetone or methyl ethyl ketone. According to an embodiment of the present invention, at least one of the above solvents may be used.

According to an embodiment of the present invention, a nitrooxybutyl ester of 2-(S)-(6-methoxy-2-naphtyl)-propanoic acid is prepared by using 2-(S)-(6-methoxy-2-naphtyl)-propanoic acid in the presence of an inert solvent. A water immiscible inert solvent may be used such as an ether (diethyl ether), a halohydrocarbon (dichloromethane) or a sulfoxide (dimethyl sulfoxide).

According to the present invention, 1,4-butanediol mononitrate is prepared by the step of performing the esterification of 1,4-bunediol by an anhydride to obtain a compound of formula (i):

RC(O)O—(CH$_2$)$_4$—OH (i), wherein R is a linear or branched C$_{1-5}$alkyl.

The anhydride may be, but not limited to, acetic acid anhydride, propionic anhydride, butyric anhydride, pentanoic anhydride or hexanoic anhydride. Preferably, the anhydride is acetic acid anhydride. According to an embodiment, the esterification of 1,4-bunediol is performed with acetic acid anhydride to form CH$_3$C(O)O—(CH$_2$)$_4$—OH.

The esterification may be performed in the presence of an acidic catalyst. The acidic catalyst may be, but not limited to, sodium bisulfate, potassium bisulfate, potassium sulfate, magnesium sulfate, sodium dihydrogen phosphate, disodium monohydrogen phosphate, potassium dihydrogen phosphate, dipotassium monohydrogen phosphate, sodium bicarbonate or potassium bicarbonate. Preferably, the acidic catalyst may be sodium bisulfate.

Further, a nitrating agent is used to nitrify the compound of formula (i) to obtain a compound of formula (ii):

RC(O)O—(CH$_2$)$_4$—ONO$_2$ (ii), wherein R is defined as the above illustration.

The reaction of the compound of formula (ii) and an inorganic alkali is performed to form 1,4-butanediol mononitrate.

According to an embodiment, the compound of formula (i) is nitrified by nitric acid.

In the present invention, the inorganic alkali may be, but not limited to, NaOH, KOH, Mg(OH)$_2$ or LiOH. According to an embodiment of the present invention, the reaction of NaOH and the compound of formula (ii) is performed to form 1,4-butanediol mononitrate.

In the present invention, the preparation of a nitrooxybutyl ester of 2-(S)-(6-methoxy-2-naphtyl)-propanoic acid by using the compound of formula (I) needs no further purification, and produces high purity (98.92%) and high yield (96.8%) of the crude product. The crude product has the outstanding e.e. (enantiomeric excess) value more than 99%.

In the present invention, the method for preparing a nitrooxybutyl ester of 2-(S)-(6-methoxy-2-naphtyl)-propanoic acid eliminates further purifications and produces high purity (98.92%) and high yield (96.8%) of the crude product. The crude product has the outstanding e.e. (enantiomeric excess) value more than 99%.

The conventional method for preparing a nitrooxybutyl ester of 2-(S)-(6-methoxy-2-naphtyl)-propanoic acid is complicated and has high cost. In contrast, the method for preparing a nitrooxybutyl ester of 2-(S)-(6-methoxy-2-naphtyl)-propanoic acid in the present invention is simple, has short reaction time (about 1.5 to 2 hours) and low cost, and eliminate racemic byproducts.

Hence, the novel compound, the use and the method for preparing the nitrooxyalkyl ester derivatives thereof in the present invention meet the requirements of the industry.

The present invention is further illustrated by, but not limited to, the following embodiments.

EMBODIMENTS

Embodiment 1

Preparation of 1,4-butanediol mononitrate

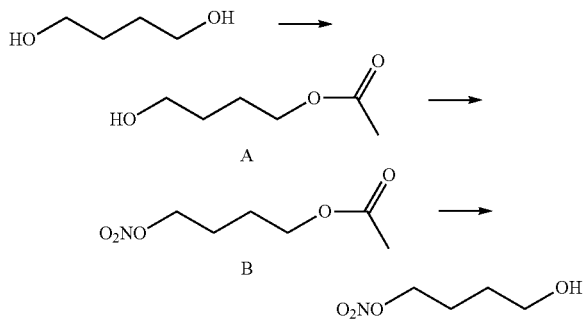

300 g (3.33 moles) of 1,4-bunediol, 600 ml of dichloromethane, 234 ml (2.49 moles) of acetic acid anhydride, 48.6 g of silicon dioxide and 17.4 g of sodium bisulfate were mixed and stirred for 2.5 hours, filtered to remove silicon dioxide, and then concentrated. The mixture was washed with water and heptane for removing 1,4-butanediol dinitrate. The aqueous layer was extracted repeatedly with isopropyl acetate to obtain the extract. Then, the isopropyl acetate layers were mixed, and the organic layer was washed with saturated sodium chloride solution for removing 1,4-bunediol, dried with sodium sulfate and concentrated, so as to obtain 228.7 g of the crude product (1.73 moles of the compound A, yield: 52%).

228.7 g (1.73 moles) of the crude product was dropped into the fuming nitric acid (535.3 g, 8.49 mmoles) in the iced bath at the temperature under 5° C. for 2.5 hours. Then, the mixture was stirred for 15 minutes. Then, this solution was poured into 2 kg of ice. The organic layer was extracted with ethyl acetate and saturated sodium bicarbonate solution, dried with sodium sulfate, and concentrated, so as to obtain 232.4 g of the crude product (1.31 moles of the compound B, yield: 75.7%).

232.4 g (1.31 moles) of the compound B, 348.6 ml of methanol, 92.96 ml of water and 62.97 g (1.57 moles) of sodium hydroxide (solid) were mixed for 30 minutes, added with 5% sulfuric acid solution (6 ml), concentrated, and then washed repeatedly with water and heptane to remove unhydrolyzed initial reactants, 1,4-butylene diacetate and 1,4-butylene dinitrate. Then, the aqueous layer was repeatedly extracted with ethyl acetate to obtain the extract. The ethyl acetate layers were mixed, washed with saturated sodium bicarbonate solution and saturated sodium chloride solution for removing 1,4-bunediol, dried with sodium sulfate, and concentrated, so as to obtain 118.1 g of the target compound (HPLC purity: 99.9%; yield: 66.6%).

Preparation of the nitrooxybutyl ester of 2-(S)-(6-methoxy-2-naphtyl)-propanoic acid

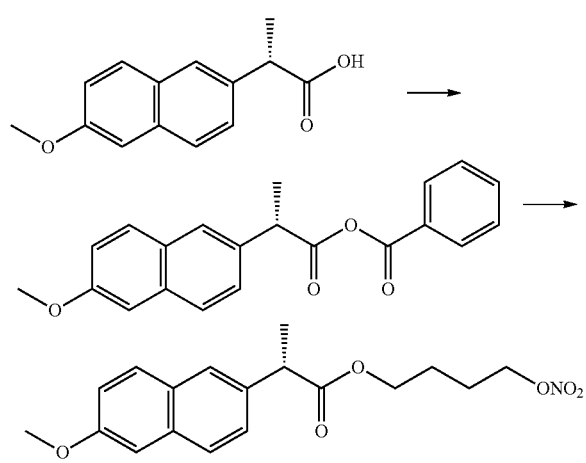

2-(S)-(6-methoxy-2-naphtyl)-propanoic acid (Naproxen, 50 g, 217 mmoles), diisopropyl ethylamine (83 ml, 477 mmoles) and dichloroethane (450 ml) were mixed, added with benzoyl chloride (31 g, 223 mmoles) at 0° C., and stirred until the reaction was completed. The reaction was monitored by thin layer chromatography.

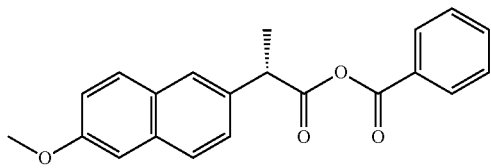 [SMILES: COc1ccc2cc([C@H](C)C(=O)OC(=O)c3ccccc3)ccc2c1]

300M Hz $^1$H NMR δ=1.70 (d, J=6.9 Hz, 3H), 3.92 (s, 3H), 4.11 (q, J=6.9 Hz, 1H), 7.13-8.14 (m, 11H)

Then, 1,4-butanediol mononitrate (29 g, 217 mmoles), 4-dimethylaminopyridine (2.6 g, 21 mmoles) and dichloromethane (50 ml) were added and stirred at 0° C. until the reaction was completed. The reaction was monitored by the TLC film. Then, the mixture was concentrated and dried for removing dichloromethane, and added with M1BE (tert-butyl methyl ether) and sodium hydroxide solution for extraction. The organic layer was extracted with hydrochloric acid, dried with sodium sulfate and concentrated to obtain 73 g of the nitrooxybutyl ester of 2-(S)-(6-methoxy-2-naphtyl)-propanoic acid (HPLC purity: 98.92%, yield: 96.8%).

400M Hz $^1$H NMR δ=1.58 (d, J=7.2 Hz, 3H), 1.60-1.65 (m, 4H), 3.84 (q, J=7.2 Hz, 1H), 3.88 (s, 3H), 4.04-4.13 (m, 2H), 4.28 (t, J=6.0 Hz, 2H), 7.11 (d, J=2.8 Hz, 1H), 7.15 (dd, J=8.8, 2.8 Hz, 1H), 7.39 (dd, J=8.8, 1.6 Hz, 1H), 7.66 (d, J=1.6 Hz, 1H), 7.70 (dd, J=8.8, 1.6 Hz, 1H); $^{13}$C NMR δ=18.2, 23.3, 24.7, 45.3, 55.1, 63.6, 72.4, 105.6, 118.9, 125.8, 126.0, 127.1, 128.8, 129.1, 133.6, 135.5, 157.6, 174.4. MS [M+H]$^+$ 348.

Embodiment 2

2-(S)-(6-methoxy-2-naphtyl)-propanoic acid (Naproxen, 1.00 g, 4.3 mmoles), diisopropyl ethylamine (1.7 ml, 9.6 mmoles) and dichloroethane (9 ml) were mixed, added with 4-methoxybenzoyl chloride

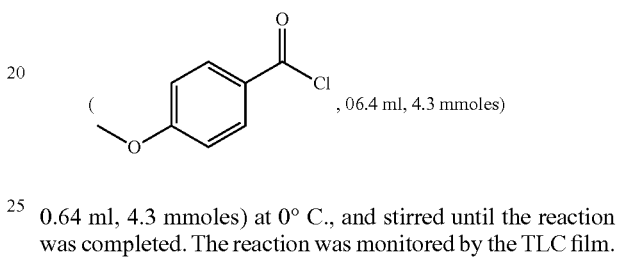

0.64 ml, 4.3 mmoles) at 0° C., and stirred until the reaction was completed. The reaction was monitored by the TLC film.

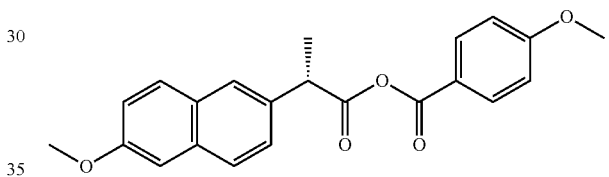

300M Hz $^1$H NM R δ=1.69 (d, J=6.9 Hz, 3H), 3.91 (s, 3H), 3.92 (s, 3H), 4.09 (q, J=7.2 Hz, 1H), 6.79-8.11 (m, 10H)

Then, 1,4-butanediol mononitrate (0.59 g, 4.3 mmoles), 4-dimethylaminopyridine (0.05 g, 0.43 mmole) and dichloromethane (1 ml) were added and stirred at 0° C. until the reaction was completed. The reaction was monitored by the TLC film. Then, the mixture was concentrated and dried for removing dichloromethane, added with MTBE and sodium hydroxide solution for extraction, dried with sodium sulfate and concentrated to obtain 1.4 g of the nitrooxybutyl ester of 2-(S)-(6-methoxy-2-naphtyl)-propanoic acid (HPLC purity: 98.94%, yield: 92.8%). (NMR and MS data were shown in Embodiment 1.)

Comparative Example 1

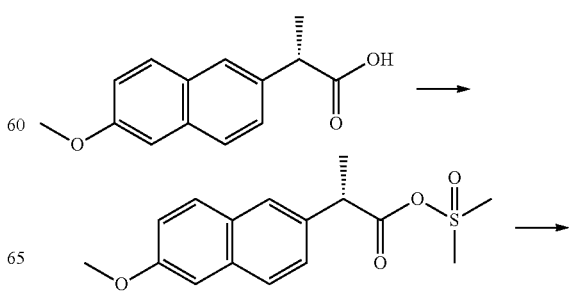

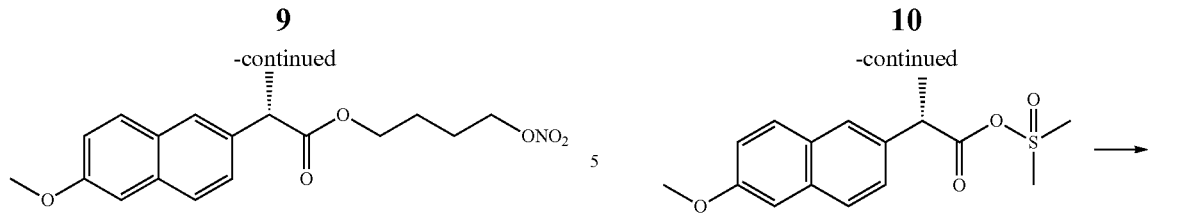

2-(S)-(6-methoxy-2-naphtyl)-propanoic acid (Naproxen, 0.50 g, 2.2 mmoles), triethylamine (1.2 ml, 8.7 mmoles) and dichloroethane (40 ml) were mixed, added with methanesulfonyl chloride (0.2 ml, 2.6 mmoles) at −25° C., and stirred for 1 hour. 1,4-butanediol mononitrate (0.35 g, 2.6 mmoles) and dichloromethane (10 ml) were slowly dropped into the mixture, and stirred for 1 hour. The organic layer was extracted with saturated sodium bicarbonate solution and water, dried with sodium sulfate and concentrated, so as to obtain 0.74 g of the nitrooxybutyl ester of 2-(S)-(6-methoxy-2-naphtyl)-propanoic acid (HPLC purity: 51.5%, yield: 50.6%).

Comparative Example 2

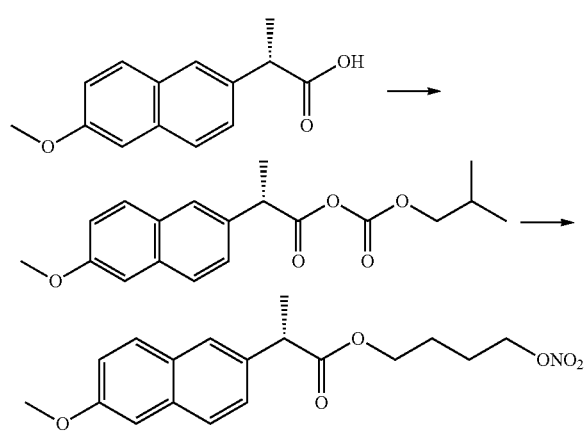

2-(S)-(6-methoxy-2-naphtyl)-propanoic acid (Naproxen, 0.50 g, 2.2 mmoles), triethylamine (0.3 ml, 2.3 mmoles) and ethyl ether (10 ml) were mixed, added with isobutyl chloroformate (0.3 ml, 2.3 mmoles) at 0° C., and stirred for 18 hours. Upon back to the room temperature, 1,4-butanediol mononitrate (0.31 g, 2.28 mmoles) and ethyl ether (10 ml) were slowly dropped into the mixture, and stirred for 18 hours. The mixture was filtered to remove the amine, extracted with saturated sodium bicarbonate solution, dried with sodium sulfate, and concentrated, so as to obtain 0.73 g of the nitrooxybutyl ester of 2-(S)-(6-methoxy-2-naphtyl)-propanoic acid (HPLC purity: 60.8%, yield: 58.9%).

Comparative Example 3

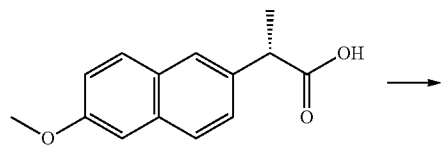

2-(S)-(6-methoxy-2-naphtyl)-propanoic acid (Naproxen, 1.00 g, 4.3 mmoles), diisopropylethylamine (1.7 ml, 9.6 mmoles) and dichloromethane (10 ml) were mixed, added with acetyl chloride (0.3 ml, 4.3 mmoles) at 0° C., and stirred for 2 hours. Then, 1,4-butanediol mononitrate (0.59 g, 4.3 mmoles), 4-dimethylaminopyridine (0.05 g, 0.43 mmole) and dichloromethane (2 ml) were added, and stirred for 2 hours. The mixture was extracted with water, saturated sodium chloride solution, saturated sodium bicarbonate solution, sodium hydroxide solution and hydrochloric acid solution, dried with sodium sulfate, and concentrated, so as to obtain 0.83 g of the nitrooxybutyl ester of 2-(S)-(6-methoxy-2-naphtyl)-propanoic acid (yield: 55.1%).

Comparative Example 4

Preparation of 1,4-butanediol dinitrate

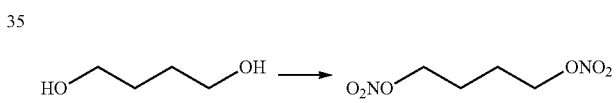

Sulfuric acid (200 ml, 3.6 moles) and dichloromethane (56 ml) were mixed, stirred and added with nitric acid (4.0 ml, 62.2 mmoles) at −15° C. for 1 to 2 minutes. Then, 1,4-butanediol (18.02 g, 200 mmoles) and nitric acid (34.8 ml, 541.2 mmoles) were slowly dropped into the mixture at the temperature under 10° C. for 45 minutes. The mixture was rinsed with dichloromethane (16 ml), and stirred for 2.5 hours. 800 g of iced water was added, and the extraction was performed with dichloromethane (360 ml). Then, the organic layer was extracted with saturated sodium bicarbonate solution and water, and dried with sodium sulfate. The reduced pressure distillation was performed at 110° C. and 355 mTorr, so as to obtain 29.74 g of the target compound (HPLC purity: 95.2%; yield: 78.6%).

Preparation of the nitrooxybutyl ester of 2-(S)-(6-methoxy-2-naphtyl)-propanoic acid

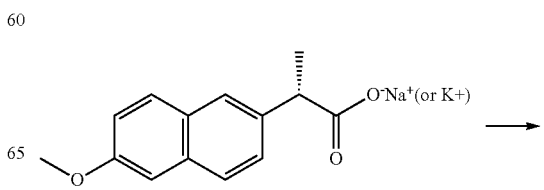

-continued

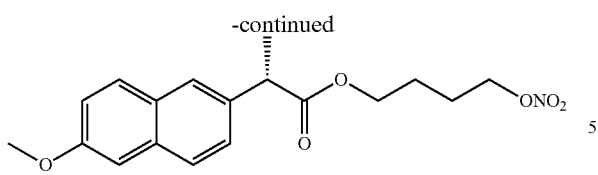

1,4-butanediol dinitrate (1.07 g, 5.95 mmoles) and DMSO (10 ml) were mixed, added with the sodium salt of 2-(S)-(6-methoxy-2-naphtyl)-propanoic acid (0.5 g, 1.982 mmoles), and stirred for 5 days. The mixture was extracted with ethyl ether and water, dried with sodium sulfate, and concentrated, so as to obtain 1.24 g of the target compound (after removing 1,4-butanediol dinitrate residues, 0.93 g; yield: 75%).

According to Embodiments 1 and 2, the preparation of nitrooxybutyl esters of 2-(S)-(6-methoxy-2-naphtyl)-propanoic acid by using the compound of formula (I) needed no further purification, and produced the product with high purity (more then 98%), high yield and outstanding optical purity (e.e. value: more than 99%).

Moreover, the conventional methods are complicated and have high cost; in contrast, the preparation of nitrooxyalkyl ester derivatives in the present invention is simple, has short reaction time (1.5 to 2 hours), has low cost and eliminates racemic byproducts. Accordingly, the novel compound, the use and the method for preparing the nitrooxyalkyl ester derivatives thereof in the present invention meet the requirements of the industry.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

The invention claimed is:

1. An anhydride derivative of 2-(S)-(6-methoxy-2-naphtyl)-propanoic acid of formula (I):

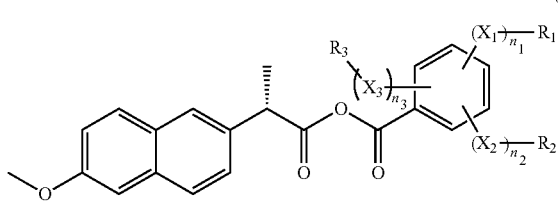

wherein $X_1$, $X_2$ and $X_3$ are independently —NR'—, —O— or —S—; $n_1$, $n_2$ and $n_3$ are independently 0 or 1; and $R_1$, $R_2$, $R_3$ and R' are independently hydrogen, a linear or branched $C_{1-10}$alkyl or halo$C_{1-10}$alkyl.

2. The anhydride derivative of 2-(S)-(6-methoxy-2-naphtyl)-propanoic acid of claim 1, wherein at least one of $X_1$, $X_2$ and $X_3$ is —O—.

3. The anhydride derivative of 2-(S)-(6-methoxy-2-naphtyl)-propanoic acid of claim 2, wherein the at least one of $X_1$, $X_2$ and $X_3$ is —O—, and $R_1$, $R_2$ or $R_3$ is methyl.

4. The anhydride derivative of 2-(S)-(6-methoxy-2-naphtyl)-propanoic acid of claim 1, wherein $n_1$, $n_2$ and $n_3$ are independently 0, and $R_1$, $R_2$, and $R_3$ are independently hydrogen.

5. A method for preparing a nitrooxybutyl ester of 2-(S)-(6-methoxy-2-naphtyl)-propanoic acid, comprising the steps of:
performing a reaction of 2-(S)-(6-methoxy-2-naphtyl)-propanoic acid and a compound of formula (a) to form a compound of formula (I)

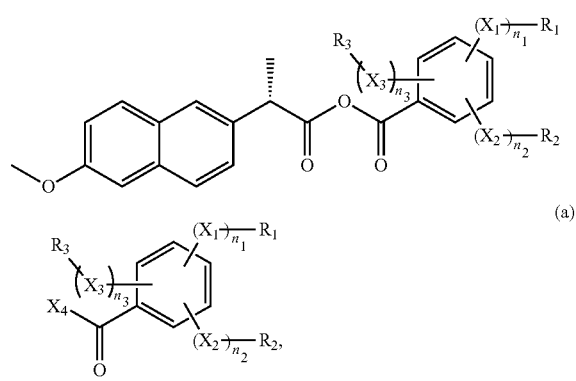

wherein $X_1$, $X_2$ and $X_3$ are independently —NR'—, —O— or —S—; $n_1$, $n_2$ and $n_3$ are independently 0 or 1; $R_2$, $R_3$ and R' are independently hydrogen, a linear or branched $C_{1-10}$alkyl or halo$C_{1-10}$alkyl; and $X_4$ is a halogen; and performing a reaction of the compound of formula (I) and 1,4-butanediol mononitrate.

6. The method of claim 5, being performed in the presence of an alkali, wherein the alkali is triethylamine, diisopropylethylamine or 4-(dimethylamino)pyridine.

7. The method of claim 5, wherein at least one of $X_1$, $X_2$ and $X_3$ is —O—.

8. The method of claim 7, wherein the compound of formula (a) is 4-Methoxybenzoyl chloride.

9. The method of claim 5, wherein the compound of formula (a) is benzoyl chloride.

10. The method of claim 5, wherein the 1,4-butanediol mononitrate is prepared by the steps of:
using a nitrating agent to nitrify a compound of formula (i) to obtain a compound of formula (ii), $$RC(O)O—(CH_2)_4—OH \quad (i)$$

$$RC(O)O—(CH_2)_4—ONO_2 \quad (ii)$$

wherein R is a linear or branched $C_{1-5}$alkyl; and
performing a reaction of the compound of formula (ii) and an inorganic alkali to obtain the 1,4-butanediol mononitrate.

11. The method of claim 10, wherein the nitrating agent of formula (i) is nitric acid.

12. The method of claim 10, wherein the inorganic alkali is sodium hydroxide.

13. The method of claim 10, wherein the compound of formula (i) is prepared from an esterification of 1,4-bunediol by an anhydride.

14. The method of claim 13, wherein the anhydride is acetic acid anhydride.

* * * * *